United States Patent [19]
Iijima

[11] Patent Number: 5,465,123
[45] Date of Patent: Nov. 7, 1995

[54] NONCONTACT TYPE TONOMETER

[75] Inventor: Hiroshi Iijima, Tokyo, Japan

[73] Assignee: Kabushiki Kaisha Topcon, Tokyo, Japan

[21] Appl. No.: 358,469

[22] Filed: Dec. 19, 1994

[30]     Foreign Application Priority Data

Dec. 20, 1993   [JP]   Japan ..................................... 5-319629

[51] Int. Cl.$^6$ ..................................................... A61B 3/14
[52] U.S. Cl. ........................... 351/208; 351/211; 128/648
[58] Field of Search ................................... 351/208, 206, 351/205, 211, 209, 221; 128/648, 645

[56]             References Cited

U.S. PATENT DOCUMENTS 4,995,393   2/1991   Katsuragi et al. ...................... 351/208

*Primary Examiner*—William L. Sikes
*Assistant Examiner*—Hung Xuan Dang
*Attorney, Agent, or Firm*—Finnegan, Henderson, Farabow, Garrett & Dunner

[57]                ABSTRACT

A noncontact type tonometer is provided which is capable of easily detecting whether optical members of the tonometer are stained with dirt or not, and easily finding which one of the optical members is stained. In the noncontact type tonometer, alignment light emitted by an alignment light source is guided to a subject's eye through an alignment light projecting optical system. Part of the alignment light reflected by the eye does not pass through a discharging nozzle and is received by a first light receiving sensor of a first alignment detecting optical system. On the other hand, the other part of the alignment light reflected by the eye passes through the discharging nozzle and is received by a second light receiving sensor of a second alignment detecting optical system. Stains on the optical members are found by a measuring device by which a quantity level of reflected alignment light received by each of the first and second sensors is detected and compared with each other. If the optical members are not stains, pulsed air is discharged from the nozzle toward the eye.

3 Claims, 4 Drawing Sheets

NONCONTACT TYPE TONOMETER

BACKGROUND OF THE INVENTION

1. Field of the Invention

This invention relates to a noncontact type tonometer for measuring the intraocular pressure of a subject's eye.

2. Description of the Prior Art

Heretofore, a noncontact type tonometer is known in which a detector detects alignment between an optical axis of a main optical system of the instrument and a visual line of a subject's eye and determines whether a working distance between a cornea of the eye and the instrument is within an allowable range or not, and then the measurement of the intraocular pressure of the eye is automatically performed based on a result obtained by the detector.

In such a tonometer, alignment is first performed between an optical axis of an anterior eye portion observing optical system and a visual line of the eye, and then pulsed air is discharged toward the cornea of the eye. The cornea is transfigured by the discharge of the pulsed air. According to the corneal transfiguration, the quantity of light reflected by the cornea increases, and thereby the quantity of light received by a light receiving sensor increases. Therefore, the intraocular pressure can be measured by measuring an increase in the quantity of the light received by the light receiving sensor.

According to the conventional tonometer, when measuring the corneal transfiguration, the pulsed air scatters tears or the like from the eye. And cases frequently occur in which part of the scattered tears adhere to optical members, such as a cover glass, an objective lens and so on, facing the eye. If the tears adherent to the optical members are not removed, they become dry and, as a result, elements other than water of the tears or fine dry particles mingled with the tears are left thereon and become stains or spots.

Therefore, as a way of finding such stains, a lens cap with a reflection plate is removably mounted in front of the optical members. A judgment on the stains is formed such that the quantity of alignment light reflected by the reflection plate is detected and compared with that of alignment light detected when the optical members have no stain.

However, in a case where a judgment whether there is any stain is formed by such a lens cap, the following faults are developed.

① If the lens cap is mounted obliquely, the reflected alignment light for alignment cannot be received accurately, and therefore a high precision in mounting the lens cap in the instrument is needed.

② In spite of the fact that the reflection plate of the lens cap is stained, cases occur where the stains on the lens cap are regarded as those on, for example, the objective lens.

③ Since a measuring process for the corneal transfiguration is different from an ascertaining process for the stains, there lies the trouble.

④ If a stain check is not performed at regular intervals of time, the measurement of the corneal transfiguration might be performed in a stained state.

⑤ If an arrangement is adopted in which a fixation target on which the eye is fixed is looked by the subject through the discharging nozzle, stains on the aforementioned optical members cannot be distinguished from stains on optical members located after the discharging nozzle which are made by an absorbing action of the nozzle after discharging the pulsed air.

SUMMARY OF THE INVENTION

It is, therefore, an object of the present invention to provide a noncontact type tonometer capable of easily judging whether optical members are stained or not, and easily finding which one of the optical members is stained.

To achieve the object, the noncontact type tonometer according to one aspect of the present invention comprises a discharging nozzle for discharging pulsed air toward a cornea of a subject's eye, an optical system for projecting alignment light emitted from an alignment light source onto the eye, a first alignment detecting optical system including a first light receiving means for receiving alignment light reflected by the eye without causing the reflected light to pass through the discharging nozzle, a second alignment detecting optical system including a second light receiving means for receiving alignment light reflected by the eye through the discharging nozzle, and a measuring means for detecting quantity levels of the light received by the first and second light receiving means.

The noncontact type tonometer according to the present invention further comprises a discriminating means for informing an operator that, when a quantity level of the reflected alignment light received by one of the first and second light receiving means is lower than a predetermined level, an optical member for guiding the reflected alignment light to the first or second light receiving means is stained.

In the above noncontact type tonometer, the quantity levels of the reflected alignment light received by the first and second light receiving means are those of the light striking the first and second light receiving means when alignment is completed.

According to the present invention, the alignment light emitted from the light source is guided to the eye through the alignment light projecting optical system. Part of the alignment light reflected by the eye does not pass through the discharging nozzle and is received by the first light receiving means of the first alignment detecting optical system, whereas the other part of the alignment light reflected by the eye passes through the discharging nozzle and is received by the second light receiving means of the second alignment detecting optical system. The stains are found by the measuring means which detects the respective quantity levels of the light received by the first and second light receiving means. If there is no stain on the optical members, pulsed air is discharged toward the cornea of the eye from the discharging nozzle.

Further, according to the present invention, the discriminating means informs an operator that the optical members for guiding the reflected alignment light to the first and second light receiving means are stained if quantity levels of the reflected alignment light received by the first and second light receiving means are lower than a predetermined level.

Further, according to the present invention, the discrimination between optical members with stains and optical members without any stain is based on the quantity levels of the light striking the first and second light receiving means when the alignment of the eye in relation to the instrument is completed.

DETAILED DESCRIPTION OF THE PREFERRED EMBODIMENTS

Embodiments of a noncontact type tonometer according to the present invention will be hereinafter described with reference to FIGS. 1 to 4.

First Embodiment

Figure 1:
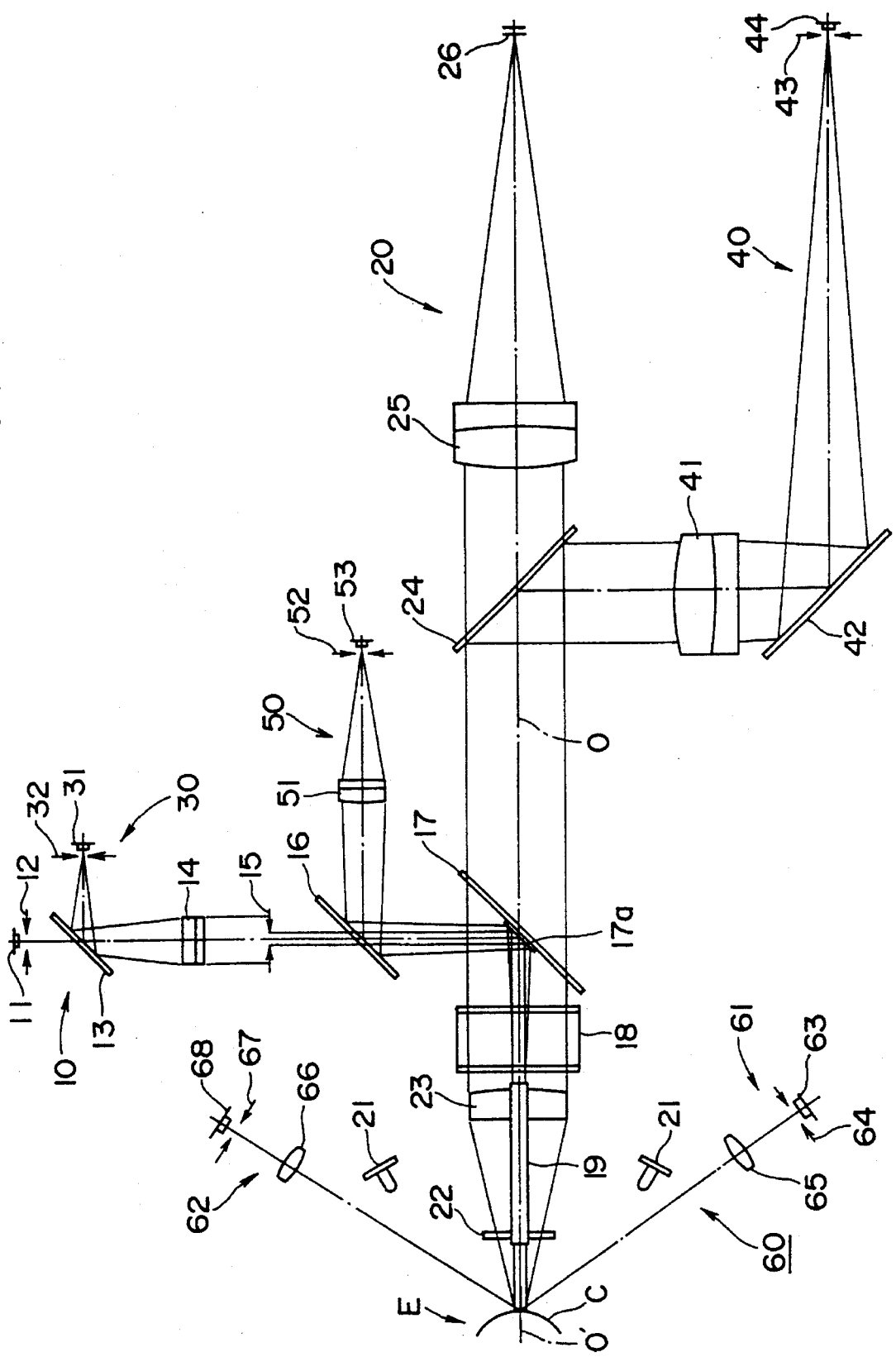
FIG. 1 is a schematic view showing optical systems of a noncontact type tonometer according to a first embodiment of the present invention, in which a subject's eye is observed.
Figure 2:
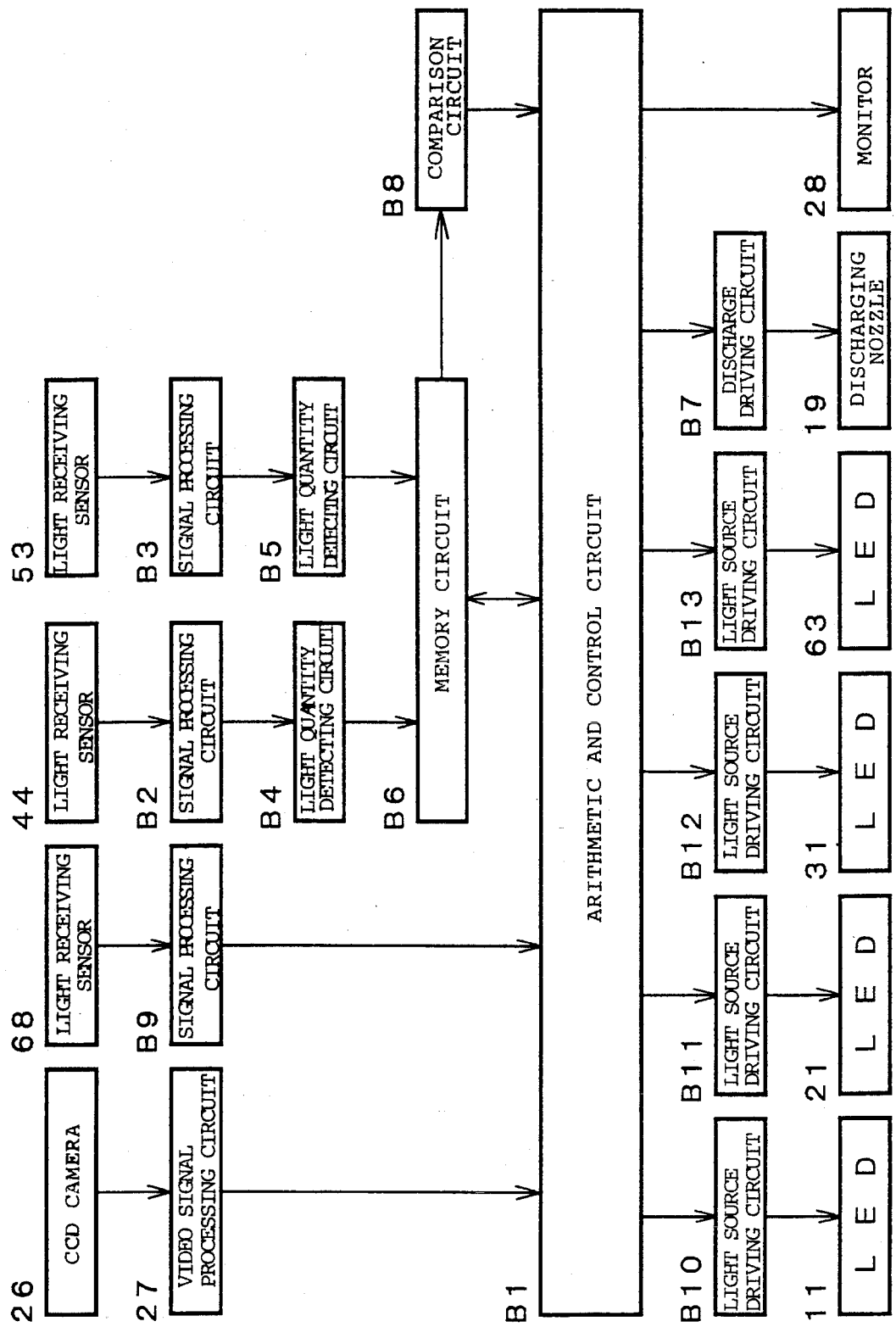
FIG. 2 is a block diagram of a control circuit of the noncontact type tonometer shown in FIG. 1.

FIGS. 1 and 2 show a first embodiment of the present invention. FIG. 1 is a schematic view of optical systems of the noncontact type tonometer according to the present invention, and FIG. 2 is a block diagram of a control circuit of the same.

In FIG. 1, 10 is an optical system for projecting a fixation target on which a subject's eye E is fixed onto an eye E. 20 is an optical system for observing the eye E and an anterior portion of the eye E. 30 is an optical system for projecting alignment light onto the eye E. 40 is a first alignment detecting optical system (hereinafter referred to as "first detecting system") for detecting a working distance between the instrument and the eye E. 50 is a second alignment detecting optical system (hereinafter referred to as "second detecting system") for detecting alignment between an optical axis O of the optical system 20 and a visual line O' of the eye E. 60 is an optical system for optically detecting the transfiguration of a cornea C of the eye E.

The optical system 10 for projecting the fixation target onto the eye E comprises a light emitting diode (hereinafter simply referred to as "LED") 11, an aperture diaphragm 12, a wavelength division filter 13, a collimator lens 14, a diaphragm 15, a half mirror 17, a mirror 17a, a chamber window 18, and a discharging nozzle 19.

The LED 11 emits visible light. The wavelength division filter 13 transmits the visible light and reflects near infrared light. The mirror 17a is mounted in the middle of the half mirror 17 and has a characteristic of total reflection.

The chamber window 18 is a frame enclosing a supplying device for supplying pulsed air to the discharging nozzle 19. The supplying device including a cylinder member is well known and, therefore, is not shown in FIG. 1.

The visible light as a fixation target emitted from the LED 11 first passes through the aperture diaphragm 12 and the wavelength division filter 13, and then the visible light is changed into parallel rays of light by means of the collimator lens 14. The parallel rays of light are changed into a diaphragm image by means of the diaphragm 15. The diaphragm image passes through the half mirror 17 and is reflected by the mirror 17a. The diaphragm image reflected by the mirror 17a passes through the chamber window 18 and the discharging nozzle 19, and is exhibited on the cornea C of the eye E. Since the visible light reflected by the cornea C is reflected by an objective lens 23, the reflected visible light is not further guided to the other optical members located after the objective lens 23.

The optical system 20 for observing the anterior eye portion includes two LEDs 21, a cover glass 22, the objective lens 23, the chamber window 18, the half mirror 17, a half mirror 24, an image-formation lens 25, and a CCD camera 26.

The two LEDs 21 emit infrared light and directly illuminate the eye E with the infrared light from right and left. The cover glass 22 is fixed to an end of the discharging nozzle 19. The objective lens 23 reflects the visible light.

The infrared light emitted from the two LEDs 21 is reflected by the eye E. The reflected infrared light passes through the cover glass 22 and is changed into parallel rays of light by means of the objective lens 23. Then, the parallel rays of light pass through the chamber window 18, the half mirror 17, and the half mirror 24 and are condensed to the image-formation lens 25. The condensed light becomes an image on the CCD camera 26.

As shown in FIG. 2, the image of the anterior eye portion formed on the CCD camera 26 is input to a video signal processing circuit 27 and is changed into digital signals. The digital signals are output to an arithmetic and control circuit B1 and then displayed on the screen of a monitor 28.

The optical system 30 for projecting alignment light includes an LED 31, an aperture diaphragm 32, the wavelength division filter 13, the collimator lens 14, the diaphragm 15, the half mirror 17, the mirror 17a, the chamber window 18, and the discharging nozzle 19.

The LED 31 emits near infrared light. The near infrared light passes through the aperture diaphragm 32 and is reflected by the wavelength division filter 13. The reflected near infrared light is changed into parallel rays of light by means of the collimator lens 14. The parallel rays of light reach the diaphragm 15 and become a diaphragm image. The diaphragm image passes through the half mirror 17 and is reflected by the mirror 17a. The reflected diaphragm image passes through the chamber window 18 and the discharging nozzle 19, and then is projected onto the cornea C of the eye E. The cornea C reflects the diaphragm image.

The first detecting system 40 includes the cover glass 22, the objective lens 23, the chamber window 18, the half mirror 17, the half mirror 24, an image-formation lens 41, a total reflection mirror 42, a diaphragm 43, and a light receiving sensor 44. The first detecting system 40 is used to detect a working distance between the instrument and the eye E at a high magnification (for example, more than ×2.0).

The alignment light reflected by the cornea C passes through the cover glass 22 and is changed into parallel rays of light by means of the objective lens 23. The parallel rays of light pass through the chamber window 18 and the half mirror 17, and then are reflected by the half mirror 24. The reflected parallel rays of light are condensed to the image-formation lens 41 and are further reflected by the total reflection mirror 42. The light reflected by the total reflection mirror 42 passes through the diaphragm 43 and is imaged on the light receiving sensor 44.

The second detecting system 50 includes the discharging nozzle 19, the chamber window 18, the mirror 17a, the half mirror 17, an image-formation lens 51, a diaphragm 52, and a light receiving sensor 53. The second detecting system 50 is used to detect the alignment of the visual line O' of the eye E with respect to the optical axis O at a low magnification (for example, less than ×1.0).

The alignment light reflected by the cornea C passes through the nozzle 19 and the chamber window 18. Then, the reflected alignment light is further reflected by the mirror 17a and the half mirror 17, and is guided to the image-formation lens 51. The image-formation lens 51 causes the reflected alignment light to pass through the diaphragm 52 and be imaged on the light receiving sensor 53.

The light receiving sensors 44 and 53 output signals to light quantity detecting circuits B4 and B5 through signal processing circuits B2 and B3, respectively. The signals output by the sensors 44 and 53 correspond to the quantity levels of the light received by the sensors 44 and 53. If the detecting circuits B4 and B5 judge that the reflected alignment light exceeds a predetermined level, they output OK signals to a memory circuit B6 to store the information about the respective quantity levels of the light received by the sensors 44 and 53.

According to the OK signals output by the detecting circuits B4 and B5, the memory circuit B6 outputs an alignment OK signal to the arithmetic and control circuit B1. When receiving the alignment OK signal, the arithmetic and control circuit B1 actuates a discharge driving circuit B7 to discharge pulsed air from the discharging nozzle 19.

On the other hand, when the measurement of the intraocular pressure of the eye E is completed, the memory circuit B6 outputs comparison signals to a comparing and calculating circuit B8. The comparison signals correspond to the stored levels of the light received by the sensors 44 and 53.

The comparing and calculating circuit B8 functions as a means for calculating a ratio between the comparison signals in order to determine whether the cover glass 22 or the chamber window 18 is stained with tears or the like scattered from the eye E and outputting the result of the calculation to the arithmetic and control circuit B1.

The arithmetic and control circuit B1 judges that the cover glass 22 is stained if a light quantity level of the first detecting system 40 is lower than a predetermined level, and judges that the chamber window 18 is stained if a light quantity level of the second detecting system 50 is lower than a predetermined level. The arithmetic and control circuit B1 functions as a discriminating means for displaying the result on the monitor 28.

A degree of the stains on the chamber window 18 is a very small compared with that of the stains on the cover glass 22. Usually, the cover glass 22 is often cleaned, and therefore a practical problem does not occur even if a judgment on the stains is formed according to the ratio of the stains between the chamber window 18 and the cover glass 22.

The optical system 60 for detecting the corneal transfiguration includes an optical system 61 for projecting detection light and an optical system 62 for receiving the detection light.

The optical system 61 projects light for detecting the corneal transfiguration onto the cornea C from an oblique direction. The obliquely projected light is used to optically detect the transfiguration of the cornea C by discharging pulsed air from the discharging nozzle 19. The detection light receiving optical system 62 obliquely receives the detection light reflected by the cornea C.

The detection light projecting optical system 61 includes an LED 63, an aperture diaphragm 64, and an objective lens 65. The detection light receiving optical system 62 includes an image-formation lens 66, a diaphragm 67, and a light receiving sensor 68. The LED 63 emits near infrared light toward the cornea C when the cornea C begins to be transfigured by the discharge of pulsed air from the discharging nozzle 19.

The detection light emitted from the LED 63 passes through the aperture diaphragm 64 and the objective lens 65, and then is reflected by the cornea C. The reflected detection light is condensed to the image-formation lens 66. The condensed light passes through the diaphragm 67 and then is imaged on the light receiving sensor 64.

The quantity of the light received by the light receiving sensor 68 increases when the cornea C beings to be transfigured. An increase signal of the quantity of the light received by the sensor 68 is output to the arithmetic and control circuit B1 through the signal processing circuit B9. Based on the increase signal, the arithmetic and control circuit B1 measures the intraocular pressure according to a known procedure.

The LEDs 11, 21, 31, and 63 emit light by actuating light source driving circuits B10, B11, B12, and B13, respectively. The emitting time and light quantity of each of the circuits B10, B11, B12, and B13 are controlled by the arithmetic and control circuit B1.

Second Embodiment

Figure 3:
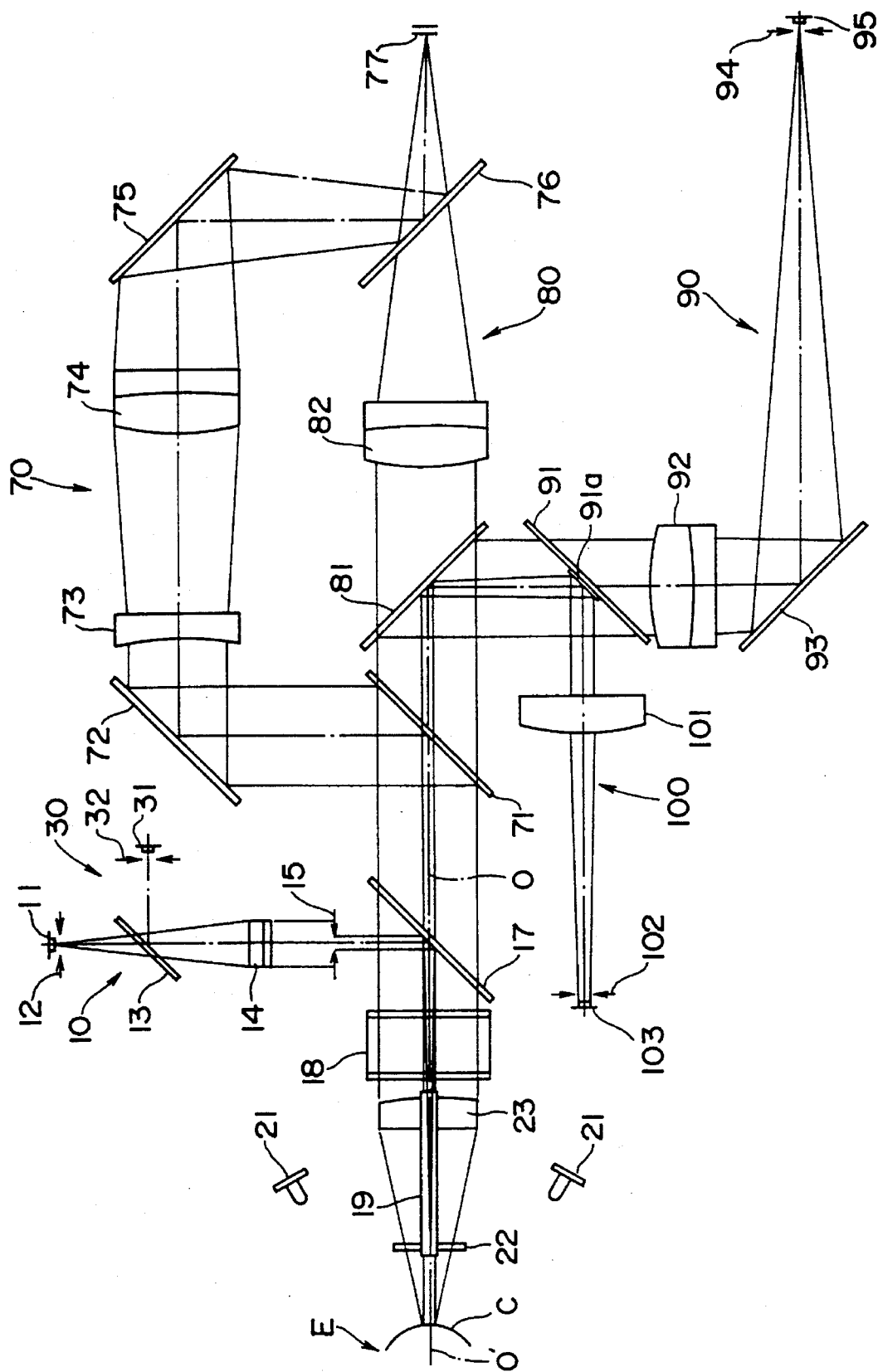
FIG. 3 is a schematic view showing optical systems of a noncontact type tonometer according to a second embodiment of the present invention, in which alignment is detected.
Figure 4:
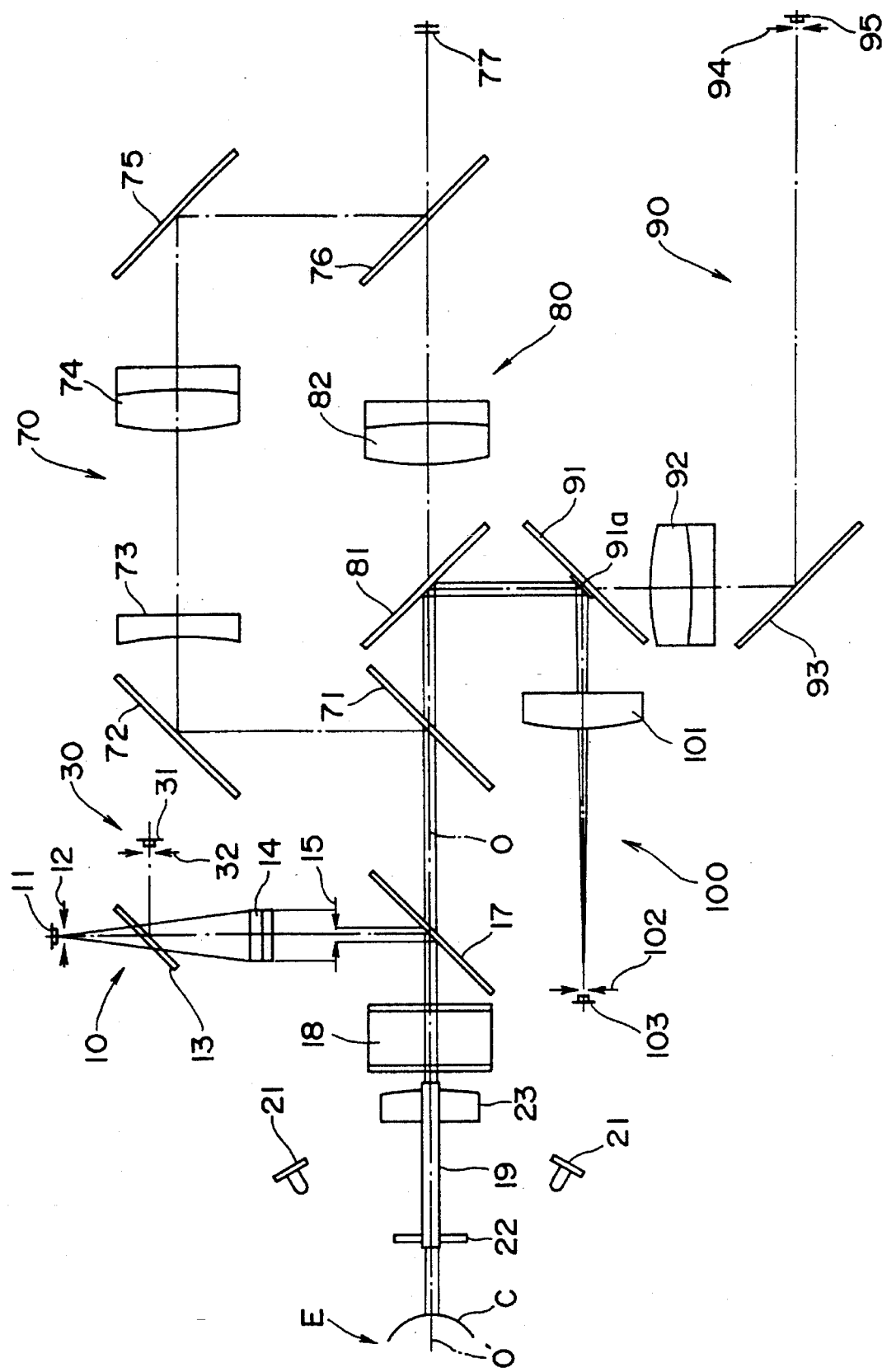
FIG. 4 is a schematic view showing the optical systems of the noncontact type tonometer according to the second embodiment of the present invention, in which the intraocular pressure of the eye is measured.

FIGS. 3 and 4 show a second embodiment of the present invention. FIG. 3 is a schematic view of optical systems of the noncontact type tonometer according to the present invention, showing a case in which an anterior portion of the eye E is observed. FIG. 4 is a schematic view of optical systems thereof, showing a case in which the intraocular pressure of the eye E is measured. In the second embodiment, the same reference numerals are given to the same components as in the first embodiment, and a description of them is omitted.

In the first embodiment, the optical system 60 for detecting the corneal transfiguration is independently disposed. However, in the second embodiment, this optical system 60 is shared with a different optical system.

In FIGS. 3 and 4, 70 is an optical system for observing the eye E and an anterior portion of the eye E. 80 is an optical system for observing an alignment state between an optical axis O of the optical system 70 and a visual line O' of the eye E. 90 is a first detecting system for detecting a working distance between the instrument and the eye E. 100 is a second detecting system for detecting alignment between the optical axis O of the optical system 20 and the visual line O' of the eye E and for optically detecting the transfiguration of the cornea C.

The optical system 70 for observing the anterior eye portion includes two LEDs 21, a cover glass 22, the objective lens 23 for reflecting visible light, the chamber window 18, the half mirror 17 (without the mirror 17a in the middle thereof), a half mirror 71, a total reflection mirror 72, a first image-formation lens 73, a second image-formation lens 74, a total reflection mirror 75, a half mirror 76, and a CCD camera 77.

The infrared light emitted from the two LEDs 21 is reflected by the eye E. The reflected infrared light passes through the cover glass 22 and is changed into parallel rays of light by means of the objective lens 23. The parallel rays of light pass through the chamber window 18 and half mirror 17, and then reach the half mirror 71. The parallel rays of light are reflected by the half mirror 71 and total reflection mirror 72, and then are condensed to the first and second image-formation lenses 73 and 74. The condensed light is reflected by the total reflection mirror 75 and half mirror 76, and then is imaged on the CCD camera 77.

The alignment observing optical system 80 includes the cover glass 22, the objective lens 23, the chamber window 18, the half mirror 17, the half mirror 71, a half mirror 81 inclined in a direction in which it crosses the half mirror 71, an image-formation lens 82, the half mirror 76, and the CCD camera 77.

The alignment light reflected by the cornea C passes through the cover glass 22 and is changed into parallel rays of light by means of the objective lens 23. The parallel rays of light pass through the chamber window 18, the half mirror 17, the half mirror 71, and the half mirror 81 and are guided to the image-formation lens 82. The image-formation lens 82 condenses the reflected alignment light and causes it to pass through the half mirror 76 and be imaged on the CCD camera 77.

The first detecting system 90 includes the optical members of the alignment observing optical system 80 ranging from the cover glass 22 to the half mirror 81, a half mirror 91 having a total reflection mirror 91a in the middle, an image-formation lens 92, a total reflection mirror 93, a diaphragm 94, and a light receiving sensor 95.

Part of the alignment light reflected by the cornea C passes through the cover glass 22 and is changed into parallel rays of light by means of the objective lens 23. The parallel rays of light pass through the chamber window 18, the half mirror 17, and the half mirror 71 and then are reflected by the half mirror 81. The rays of light reflected by the half mirror 81 pass through the half mirror 91 and are condensed to the image-formation lens 92. The condensed light is reflected by the total reflection mirror 93. The reflected light passes through the diaphragm 94 and is imaged on the light receiving sensor 95.

The second detecting system 100 includes the discharging nozzle 19, the chamber window 18, the half mirrors 17, 71, 81, the total reflection mirror 91a, an image-formation lens 101, a diaphragm 102, and a light receiving sensor 103.

The other part of the alignment light reflected by the cornea C passes through the discharging nozzle 19, the chamber window 18, and the half mirrors 17 and 71, and then is reflected by the half mirror and mirror 91a. The reflected light is guided to the image-formation lens 101. The image-formation lens 101 causes the light to pass through the diaphragm 102 and be imaged on the light receiving sensor 103.

The light receiving sensors 95 and 103 having the same functions as the light receiving sensors 44 and 53, respectively, detect the alignment and the stains on the optical members.

On the other hand, the optical members of the target projecting optical system 10 ranging from the LED 11 to the discharging nozzle 19 function as an optical system for projecting the light for detecting the corneal transfiguration, as shown in FIG. 4.

That is, the visible light emitted from the LED 11 passes through the target projecting optical system 10 and is projected onto the cornea C. The detection light reflected by the cornea C passes through the discharging nozzle 19, the chamber window 18, and the half mirrors 17, 77, and then is reflected by the half mirror 81 and mirror 91a. The visible light reflected by the mirror 91a reaches the image-formation lens 101. The image-formation lens 101 causes the reflected visible light for detecting the corneal transfiguration to pass through the diaphragm 102 and be imaged on the light receiving sensor 103. The light receiving sensor 103 measures the intraocular pressure in the same way that the light receiving sensor 68 does.

Concerning the optical members which might receive tears or the like directly from the eye E or indirectly therefrom by the absorption of the discharging nozzle 19, the noncontact type tonometer according to the present invention can determine whether these optical members are stained or not and can easily find which one of the optical members is stained. In addition, since the noncontact type tonometer can detect stains generated in the usual measurement, the stains can be certainly detected and cleaned relatively soon after the generation of the stains.

Further, according to the invention, since the stains on the optical member (the chamber window 18) located after the discharging nozzle 19 can be detected, a bright fixation target can be always shown to the subject.

Further, according to the invention, the respective quantities of light received by the first and second light receiving sensors are detected and compared with each other, and therefore the stains can be detected in spite of a difference between reflection factors of the cornea C.

Further, according to the invention, the first detecting system 40 for detecting a working distance has a high magnification, whereas the second detecting system 50 for detecting the alignment of the optical axis O with respect to the visual line O' has a low magnification. Accordingly, measurement errors caused by the difference of the reflection factors the cornea C can be reduced.

What is claimed is:

1. A noncontact type tonometer comprising:

a discharging nozzle for discharging pulsed air toward a cornea of a subject eye;

an optical system for projecting alignment light emitted from an alignment light source onto said eye;

a first alignment detecting optical system comprising first light receiving means for receiving alignment light reflected by said eye without causing said reflected alignment light to pass through said discharging nozzle;

a second alignment detecting optical system comprising second light receiving means for receiving alignment light reflected by said eye through said discharging nozzle; and means for detecting a quantity level of light received by each of said first and second light receiving means.

2. A noncontact type tonometer according to claim 1, further comprising means for informing an operator that, if one of quantity levels of reflected light received by said first and second light receiving means is less than a predetermined level, an optical member for guiding the reflected light to said first or second light receiving means having the quantity level less than the predetermined level is stained.

3. A noncontact type tonometer according to claim 2, wherein the quantity level of the reflected alignment light received by each of said first and second light receiving means is that of the reflected alignment light received when alignment is completed.

* * * * *